United States Patent [19]

Soukup

[11] Patent Number: 5,020,545
[45] Date of Patent: Jun. 4, 1991

[54] CARDIAC LEAD ASSEMBLY AND METHOD OF ATTACHING A CARDIAC LEAD ASSEMBLY

[75] Inventor: Thomas M. Soukup, Lake Jackson, Tex.

[73] Assignee: Siemens-Pacesetter, Inc., Sylmar, Calif.

[21] Appl. No.: 468,527

[22] Filed: Jan. 23, 1990

[51] Int. Cl.$^5$ .............................................. A61N 1/05
[52] U.S. Cl. .............................. 128/785; 128/419 P; 128/642; 128/786
[58] Field of Search .................... 128/419 P, 784, 785, 128/786, 642

[56] References Cited

U.S. PATENT DOCUMENTS

| | | | |
|---|---|---|---|
| 3,416,534 | 12/1968 | Quinn | 128/418 |
| 4,207,903 | 6/1980 | O'Neill | 128/785 |
| 4,287,896 | 9/1981 | Grigorov et al. | 128/786 |
| 4,452,254 | 6/1984 | Goldberg et al. | 128/785 |
| 4,862,887 | 9/1989 | Weber et al. | 128/642 |

FOREIGN PATENT DOCUMENTS 0282047  9/1988  European Pat. Off. ............ 128/785

OTHER PUBLICATIONS

"Troubleshooting Pacing Problems" Cardiac Pacemakers, Inc., 1980, pp. 15-22.

Primary Examiner—Francis Jaworski
Assistant Examiner—Scott M. Getzow
Attorney, Agent, or Firm—Malcolm J. Romano

[57] ABSTRACT

A cardiac lead assembly for use with a heart pacemaker. The assembly has an inner electrode with a corkscrew tip, and an electrode housing which can be comprised of a second electrode. A conductor is connected to the inner electrode for supplying electricity thereto and is comprised of a tubular coil. The inner electrode can be manually moved longitudinally relative to the electrode housing by a stylet. The inner electrode and the housing cooperate to prevent axial rotation of the inner electrode at a first longitudinal position, but allow rotation at a second longitudinal position. The first conductor coil can be suitably twisted such that upon movement of the inner electrode to the second position the coil can automatically axially rotate the inner electrode to screw the corkscrew tip into a patient's heart.

18 Claims, 2 Drawing Sheets

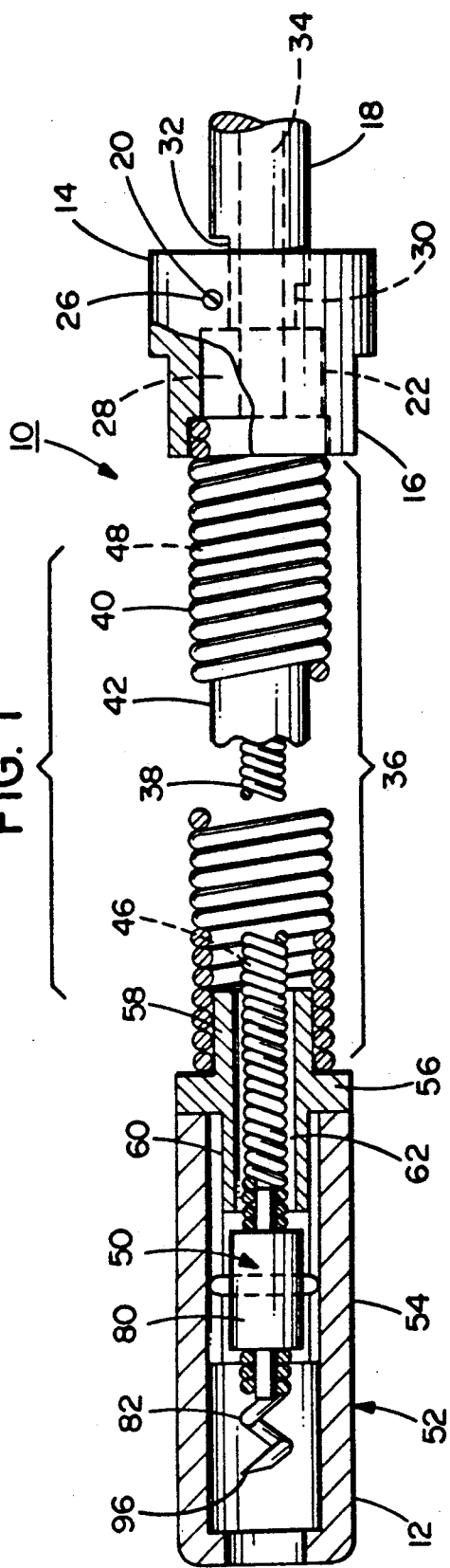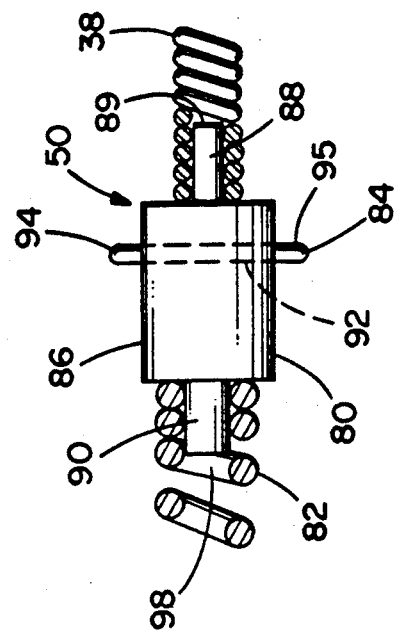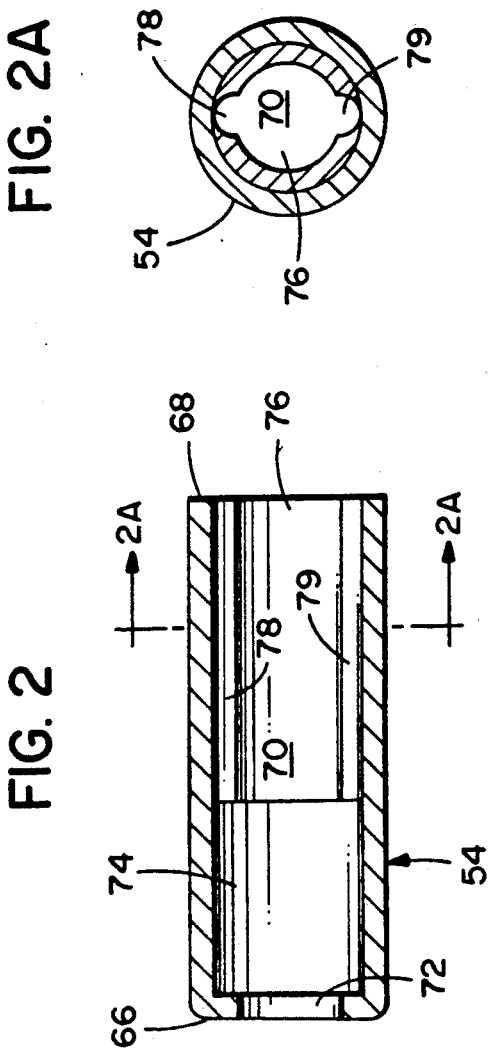

CARDIAC LEAD ASSEMBLY AND METHOD OF ATTACHING A CARDIAC LEAD ASSEMBLY

BACKGROUND OF THE INVENTION

1. Field of the Invention

This invention relates to electrical electrodes and, more particularly, to a cardiac lead assembly and a method of attaching a cardiac lead assembly to a patient's heart.

2. Prior Art

For some time, electrical leads have been used to conduct pacing signals from a pacemaker to the heart of a living subject. Such cardiac electrodes typically terminate in an electrode tip which must be surgically implanted in the heart to deliver the desired pacing signals to an appropriate portion of the heart. Screw-in electrodes can be implanted in the heart with relatively little trauma to the heart muscle. However, even with screw-in electrodes, accurate manual implantation can be difficult due to movement of the heart, and this movement can result in undesired laceration of the heart by the electrode before the electrode has become embedded in the heart.

Lacerations of the type described above can result in the formation of undesirable scar tissue near or immediately adjacent to the electrode. Such scar tissue tends to increase the voltage of the pacing signal required to pace the heart properly. This increased voltage in turn reduces the life of batteries used to power the associated pacemaker.

In addition, many commonly used screw-in electrodes use perforated, fabric skirts near the screw-in electrode as an aid in fastening the electrode to the heart. In use, these fabric skirts serve as bonding sites at which heart tissues can engage the electrode to hold the electrode firmly to the heart. Such bonding skirts present important disadvantages in that they do not significantly help to secure the electrode to the heart for some period of time after the electrode has been implanted in the heart. This is because heart tissues do not grow into and around the fabric skirt until a period of time ranging from several days to weeks has elapsed. During this period of time, prior to the attachment of the skirt to the heart, it is the screw-in electrode itself which holds the electrode in place.

Once fabric skirts of the type described above have become embedded in heart tissue, the electrode often cannot be removed from the heart without cutting the skirt and associated heart tissue from the heart. Thus, the removal of the electrode is a surgical procedure which serves further to traumatize the heart and can result in the formation of additional scar tissue.

Many conventional screw-in electrodes have electrodes approximately six millimeters in length. However, it has been established that the wall thickness of the muscle layer of the apex of the left ventricle of many human subjects is at its thinnest point less than two millimeters in thickness. Thus, there is a very real danger that screw-in electrodes of the conventional type may perforate the ventricular wall.

U.S. Pat. No. 4,452,254 to Goldberg et al. discloses a cardiac lead assembly with an elongatable coil spring which serves to connect a screw-in electrode tip with a connector. A surgeon uses the coil spring to first stretch and then release the coil to snap forward the electrode tip at the heart of a patient to penetrate the surface of the heart. Goldberg et al. discloses that this type of slingshot method preferably also imparts an angular momentum to the electrode tip. Other types of pacing leads include active fixation leads such as with pronged tips and endocardial pinch-on tips, and passive fixation leads such as with helical coil tips, tined tips, balloon tips and porous tips.

One major problem with devices known in the prior art is that angular motion or rotation of an electrode tip, such as a screw-in tip, is generally provided through the use of a stylet, which is manually turned by a surgeon, or by manually rotating the lead conductor with the lead body. This method and the slingshot method disclosed in Goldberg et al. do not provide an automatic and reliably controllable angular rotation of a tip for attachment to a patient's heart in a relatively quick manner and with relatively little trauma to the heart.

It is therefore an objective of the present invention to provide an improved cardiac lead assembly and method of attaching the same that overcomes disadvantages in the prior art devices as well as provide other advantages.

SUMMARY OF THE INVENTION

The foregoing problems are overcome and other advantages are provided by a cardiac lead assembly having an inner electrode that can be manually longitudinally moved by a surgeon and can automatically rotate upon reaching a predetermined longitudinal position and a method of attaching the assembly to a patient's heart.

In accordance with one embodiment, a cardiac lead assembly is provided comprising a first conductor, a first electrode, a second electrode and a torsion coil. The first electrode has a conduit therein with a lock groove in the conduit. The first electrode is connected to a distal end of the first conductor. The second electrode has a fixation bobbin, a fixation screw fixably connected to the fixation bobbin and a lock pin extending from the fixation bobbin. The second electrode is longitudinally moveable in the first electrode conduit with a first position wherein the lock pin and the lock groove substantially prevent axial rotation of the second electrode relative to the first electrode, and a second position wherein the second electrode is capable of axial rotation relative to the first electrode. The torsion coil has a first distal end fixedly connected to the fixation bobbin and an opposite second end. The coil ends are axially rotatable relative to each other for storing torsional potential energy while the second electrode is at the first position, and for releasing stored torsional energy to axially rotate the second electrode at the second position. The coil has a coil channel therein for passage of a stylet therethrough for manually pushing and longitudinally moving the second electrode from the first position to the second position such that, upon movement of the second electrode to the second position, the stored torsional energy can be, at least partially, released for axially rotating the coil first end and second electrode, a tip of the second electrode fixation screw can penetrate a surface of a patient's heart, and the fixation screw can automatically screw the second electrode into the patient's heart as the second electrode rotates thereby embedding and fixing the lead of the heart.

In accordance with another embodiment of the present invention a cardiac lead assembly is provided comprising a first electrode, a second electrode, means for conducting electricity, means for allowing access to a rear end of the second electrode, and means for automatically axially rotating the second electrode. The second electrode is at least partially located in the first electrode and has a corkscrew-type fixation tip. The means for conducting electricity is capable of conducting electricity to and from the first and second electrodes. The means for allowing access to a rear end of the second electrode allows access by a stylet for manually pushing the second electrode and longitudinally moving the second electrode relative to the first electrode. The means for automatically axially rotating the second electrode can do so upon movement of the second electrode from a first longitudinal position to a second longitudinal position to thereby automatically screw the fixation tip into a heart of a patient.

In accordance with another embodiment of the present invention, a cardiac lead assembly is provided comprising a first electrode, an electrode housing, a first conductor, means for manually longitudinally moving the first electrode, and means for automatically axially rotating the first electrode. The first conductor is connected to the first electrode. The means for manually longitudinally moving the first electrode can do so relative to the electrode housing. The means for rotating can automatically axially rotate the first electrode relative to the electrode housing.

In accordance with another embodiment of the present invention, a cardiac lead assembly is provided having a first electrode, a first conductor, a second electrode, a second conductor, and means for moving the second electrode. The first conductor is connected to the first electrode. The second conductor is connected to the second electrode. And the means for moving can move the second electrode relative to the first electrode.

In accordance with one method of the present invention, a method is provided for attaching an electrode lead to a patient's heart. The method generally comprises steps of providing a cardiac lead assembly which comprises a first electrode, a second electrode with a screw tip, means for automatically axially rotating the second electrode, and means for restraining axial rotation of the second electrode; pointing a distal end of the assembly at a selected portion of a patient's heart; longitudinally moving the second electrode relative to the first electrode manually with a stylet to a location wherein the second electrode screw tip contacts a patient's heart and the means for restraining axial rotation of the second electrode is disengaged; and automatically axially rotating the second electrode such that the second electrode screw tip can penetrate a surface of the heart and screw the second electrode into a fixedly embedded position in the heart.

BRIEF DESCRIPTION OF THE DRAWINGS

The foregoing aspects and other features of the invention are explained in the following description, taken in connection with the accompanying drawings, wherein:

FIG. 1 is a partial cross-sectional view of a cardiac lead assembly incorporating features of the present invention.

FIG. 2 is a cross-sectional view of the outer electrode of the assembly shown in FIG. 1.

FIG. 2A is a cross-sectional view of the outer electrode shown in FIG. 2 taken along line 2A-2A.

FIG. 3 is a partial cross-sectional side view of the inner electrode of the assembly shown in FIG. 1.

DETAILED DESCRIPTION OF THE INVENTION

Figure 4:
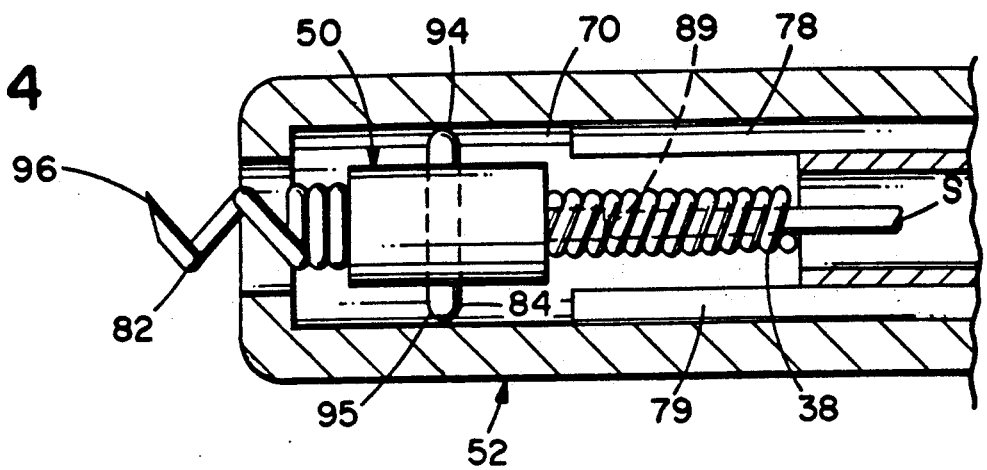
FIG. 4 is a schematic cross-sectional side view of the distal end of the assembly shown in FIG. 1 at an extended position.

Referring to FIG. 1, there is shown a partial cross-sectional view of a cardiac lead assembly 10 incorporating features of the present invention. While the following description is with reference to the embodiments shown in the drawings, it should be understood that the present invention is capable of use in various forms, in various types of applications, and in various methods of use. In addition, any suitable size, shape or type of materials can be used as elements in an embodiment of the present invention.

In the embodiment shown, the assembly 10 generally comprises an elongate shape having a distal end 12 and a proximal end 14. In the embodiment shown, the proximal end 14 comprises a slip ring 16, a connector member 18, and a locking pin 20. The slip ring 16 has a general tubular shape with an inner channel 22 and a locking pin aperture 26 passing through the slip ring 16 into the inner channel 22. The locking pin aperture 26 is generally suitably sized and shaped to allow the locking pin 20 to pass therethrough and be fixedly mounted to the slip ring 16. The connector member 18 generally comprises a first end 28, a circular depression 30 surrounding a portion of the connector member 18, a keyed portion 32 extending along a side portion of the connector member length from the circular depression 30 on one side of the connector member 18, and a central aperture or channel 34 for passage of a stylet therethrough. The connector member 18 is adapted for limited longitudinal movement or movement along its center axis and limited axial rotational movement or annular rotation depended upon the location of the connector member 18 in the slip ring inner channel 22. The movement between the connector member 18 and the slip ring 16 will be further described below in addition to their functions.

In the embodiment shown, located between the distal end 12 and proximal end 14, is a center shaft portion 36 generally comprised of an inner conductor 38, an outer conductor 40, an inner insulator 42 and an outer insulator (not shown). The inner conductor 38 is generally comprised of a coiled wire which forms a general tubular shape having a center conduit 46 therethrough. The outer conductor 40 is also generally comprised of a coiled conductor wire forming a general tubular shape with a center conduit 48 passing therethrough. In the embodiment shown the inner conductor 38 is coaxially located relative to the outer conductor 40 inside the outer conductor center conduit 48 with the inner insulator 42 therebetween. The outer insulator (not shown) is generally comprised of a dielectric material and substantially spans the entire length of the cardiac lead assembly 10. The proximal end of the inner conductor 38 is fixedly connected to the connector member 18 with its center conduit 46 suitably aligned with the central channel 34 in the connector member 18. The outer connector 40 has its proximal end fixedly connected to the slip ring 16. The inner insulator 42, although disposed between the inner conductor 38 and outer conductor 40, does not inhibit movement of the inner conductor 38 as will be described below.

The distal end 12, in the embodiment shown, generally comprises an inner electrode 50 and an outer electrode 52. The distal end of the inner conductor 38 is electrically and mechanically connected to the inner electrode 50. The distal end of the outer conductor 40 is electrically and mechanically connected to the outer electrode 52. In the embodiment shown, the outer conductor 40 is suitably strong to prevent axial rotational movement between the slip ring 16 and outer electrode 52. In the embodiment, the outer electrode 52 is generally comprised of an electrode body 54 and a back stop 56. The back stop 56 is generally provided to limit the rearward location or movement of the inner electrode 50 and for connecting the distal end of the outer conductor 40 thereto. The back stop 56 has a ledge 58, a stop extension 60 and a center channel 62 passing therethrough. In the embodiment shown, the distal portion of the outer conductor 40 is slid over the ledge 58 and fixedly attached thereto by suitable means such as a crimp sleeve (not shown). The back stop center channel 62 is suitably sized and shaped for passage of a portion of the inner conductor 38 therethrough. Referring also to FIGS. 2 and 2A, the electrode body 54 is generally comprised of an electrically conductive material and has a generally tubular shape with a forward end 66 and a rearward end 68. Passing between the rearward end 68 and forward end 66 is a center channel or conduit 70. The center channel 70 forms an aperture 72 in the forward end 66, an enlarged area 74 proximate the front end aperture 72, and has a grooved channel portion 76 between the rearward end 68 and the enlarged area 74. In the embodiment shown, the groove channel portion 76 comprises two grooves 78 and 79 extending into the electrode body 54 along the entire length of the groove channel portion 76. In the embodiment shown, the two grooves 78 and 79 are located opposite each other and are comprised of straight grooves longitudinally along the electrode body 54.

Referring now also to FIG. 3, in the embodiment shown, the inner electrode 50 is generally comprised of a fixation bobbin 80, a fixation screw 82 and a lock pin 84. The fixation bobbin 80, in the embodiment shown, generally comprises a center portion 86, a rear end extension 88, a front end extension 90, and a lock pin channel 92. Suitable means are provided to electrically insulate the electrically conductive fixation screw 82 and inner conductor 38 from the outer electrode 52. In a preferred embodiment of the present invention, the center portion 86 and the lock pin 84 are comprised of dielect material and may be formed as one member with a channel therethrough for passage of an electrically conductive member comprising the rear end extension 88 and front end extension 90. In the embodiment shown, the rear end extension 88 is generally provided for connecting a distal end of the inner conductor 38 to the fixation bobbin 80. However, any suitable means may be provided for connecting the inner conductor 38 to the fixation bobbin 80 or fixation screw 82. In the embodiment shown, the rear end extension 88 extends partially into the distal end of the inner conductor center conduit 46 with the inner conductor 38 fixedly connected thereto. In the embodiment shown, the lock pin 84 has a first end 94 and a second end 95 that laterally extend away from the fixation bobbin 80 in opposite directions. The lock pin ends 94 and 95 are suitably sized and shaped to be positionably located in the electrode body grooves 78 and 79 as will be further described below. The fixation screw 82, in the embodiment shown, is generally comprised of a coiled conductor forming a general corkscrew-type configuration with a leading tip 96 (see FIG. 1) intended to penetrate and bore into a patient's heart muscle. The fixation screw 82 has a general tubular shape with a center channel 98. The front end extension 90 of the fixation bobbin 80 is suitably sized and shaped to be received inside the fixation screw center channel 98 such that the fixation screw 82 can be fixedly connected to the fixation bobbin 80. However, any suitable means may be provided for fixedly connecting the fixation screw 82 to the fixation bobbin 80 or distal end of the inner conductor 38.

In the embodiment shown in FIG. 1 (and FIGS. 2-4), the inner electrode 50 is adapted for both longitudinal and axial movement relative to the outer electrode 52. Generally, the inner electrode 50 can be moved in a longitudinal direction towards the forward end 66 of the electrode body 54 by a surgeon using a stylet passed through the assembly 10 from the proximal end 14 through the inner conductor center conduit 46 to a rear face 89 on the fixation bobbin rear extension 88. Generally, in the home position as shown in FIG. 1, the inner electrode 50 is in a rearward most position with the fixation bobbin 80 substantially located in the grooved channel portion 76 of the electrode body channel 70 and lock pin first and second ends 94 and 95 being located in the electrode body grooves 78 and 79. In the home position shown, the lock pin 84 and grooves 78 and 79 cooperate to restrain or prevent axial rotation of the inner electrode 50 relative to the outer electrode 52. As shown with reference to FIG. 4, the inner electrode 50 can be longitudinally moved or pushed by a stylet S in the electrode body channel 70 from its home position to an extended position.

As the inner electrode 50 is advanced, the leading tip 96 of the fixation screw 82 passes through the aperture 72 in the outer electrode body 54 and can contact and penetrate the surface of a patient's heart. Also, as the inner electrode 50 is advanced, the ends 94 and 95 of the lock pin 84 can exit the grooves 78 and 79 in the grooved channel portion 76 of the electrode body 54 into the enlarged area 74. When the ends 94 and 95 of the lock pin 84 enter the enlarged area 74, the inner electrode 50 is no longer restrained from axial rotation by the outer electrode 52. The inner conductor 38 can then release stored torsional potential energy as will be described below.

Generally, before an operation begins or alternatively just prior to intended attachment of the lead assembly to a patient's heart, the surgeon will grasp the proximal end 14 of the lead assembly 10 and pull on the connector member 18 relative to the slip ring 16. This action moves the connector member 18 relative to the slip ring 16 with the locking pin 20 sliding along the keyed portion 32 into the circular depression 30. The outer electrode back stop 56 can stop the inner electrode 50 from being pulled rearward by the inner conductor 38. Because the inner conductor 38 is provided in the shape of a coil, the coil can lengthen slightly to allow the connector member 18 to move relative to the inner electrode 50. With the circular depression 30 of the connector member 18 aligned with the locking pin 20, the connector member 18 is substantially free to axially rotate relative to the slip ring 16. The surgeon can now axially rotate the connector member 18 in a predetermined direction for a predetermined number of rotations such as five or six. A suitable ratchet mechanism (not shown) can also be provided to prevent inadvertent turning of the connector member 18 in a direction other than the predetermined direction. Because the inner electrode 50 is prevented from axially rotating while in its home position, due to the cooperating engagement of the lock pin 84 and grooves 78 and 79, and the outer electrode 52 is prevented from axial rotation relative to the slip ring 16 by the outer conductor 40, the connector member 18 is axially rotated relative to the inner electrode 50. Generally, this can be accomplished due to the fact that the inner conductor 38 has a coil configuration which can absorb the effects of the offset axial rotation between its proximal and distal ends. In the embodiment shown, the surgeon would rotate the connector member 18 in a clockwise direction because the fixation screw 82 is coiled in a clockwise advancing direction. If the fixation screw were provided in a counterclockwise advancing direction, then the surgeon would rotate the connector member 18 in a counterclockwise direction. In the embodiment shown, the inner electrode 50 being rotationally stationary relative to outer electrode and slip ring, the inner conductor 38 expands or uncoils slightly with the resultant creation of stored torsional potential energy in the inner conductor 38.

After the surgeon completes the predetermined number of rotations of the connector member 18, the surgeon pushes the connector member forward, or releases it to be pulled forward by the inner conductor 38, with the locking pin 20 being received in the connector member keyed portion 32. Thus, with the inner electrode 50 held in the outer electrode 52, the connector member 18 held in the slip ring 16, and the outer conductor 40 fixedly connected between the slip ring 16 and the outer electrode 52, the stored torsional potential energy in the coil of the inner conductor 38 is prevented from being released until the surgeon advances the inner electrode 50 by use of a stylet. Generally, after the surgeon as prepared the lead assembly 10 by preloading the inner conductor as described above, he can position the distal end 12 proximate a patient's heart with the forward end 66 of the outer electrode 52 thereagainst, and insert a stylet S into the assembly 20. The stylet S can be passed through the connector member central channel 34, into the center conduit 46 of the inner conductor 38, and against the rear face 89 of the fixation bobbin 80. By pushing on the stylet S, the surgeon can longitudinally advance the inner electrode 50 relative to the outer electrode 52, the inner conductor 38 lengthening slightly, until the ends 94 and 95 of the lock pin 84 exit the grooves 78 and 79 of the outer electrode 52. Once released from the axial rotational restriction of the grooves 78 and 79, the inner electrode 50 can automatically axially rotate due to the stored torsional energy in the coiled inner conductor 38. The release of the stored torsional energy axially rotates the inner electrode 50 relative to the outer electrode 52. Because the connector member 18 was rotated by the surgeon in a clockwise direction, in the embodiment shown, the inner conductor 38 rotates the inner electrode 50 in a clockwise direction which in turn rotates the fixation screw 82 in a clockwise direction. Because the tip 96 of the fixation screw 82 having first contacted or penetrated the surface of a patient's heart prior to release of the stored torsional energy in the inner conductor 38, as the fixation screw 82 axially rotates or turns, the screw automatically screws itself into the heart of the patient. In a preferred embodiment, the automatic screwing of the fixation screw results in the fixation bobbin 80 or lock pin 84 coming to rest against the inside of the electrode body 54 to hold the outer electrode 52 against the surface of the patient's heart.

Figure 5:
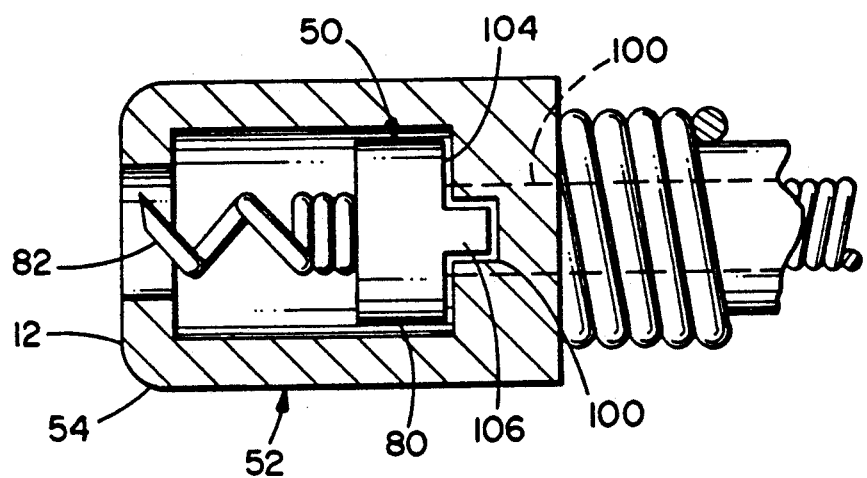
FIG. 5 is a schematic cross-sectional side view of a distal end of an alternate embodiment of the present invention.

Referring to FIG. 5, there is shown an alternate embodiment of the present invention wherein the distal end 12 has an outer electrode body 54 with an interior slot 100 and rear end channel 102. The inner electrode 52 has a bobbin 80 with a slot key 106 on its rear end 104. The key 106 and slot 100 prevent the inner electrode 50 from axially rotating relative to the outer electrode 5 until the inner electrode 50 is advanced relative to the outer electrode 52 by a stylet passed through the end channel.

Figure 6A:
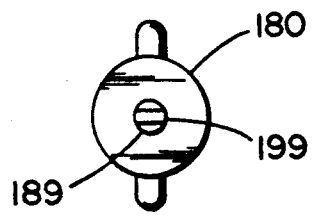
FIG. 6A is a plan rear view of an inner electrode bobbin of an alternate embodiment of the present invention.
Figure 6B:
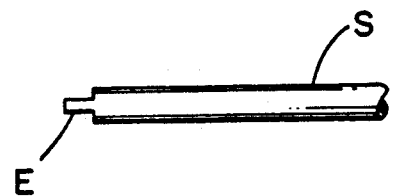
FIG. 6B is a schematic side view of a stylet having a distal tip for cooperation with the rear end of the bobbin shown in FIG. 6A.

Referring to FIGS. 6A and 6B, the rear end of a fixation bobbin 180 for an alternate embodiment, and a partial side view of the distal end of a stylet S are shown, respectively. The fixation bobbin 180 is substantially similar to the bobbin 80 shown in FIG. 3, but has a rear face 189 with a key slot 199. The stylet S has a distal tip with a key extension E that can be received in the bobbin slot 199. With this type of configuration, although the inner conductor 38 can automatically turn the inner electrode, the surgeon can control the rate at which the inner conductor turns the inner electrode. In addition, the stylet can be used to further turn the inner electrode relative to the outer electrode if desired or necessary.

Figure 7:
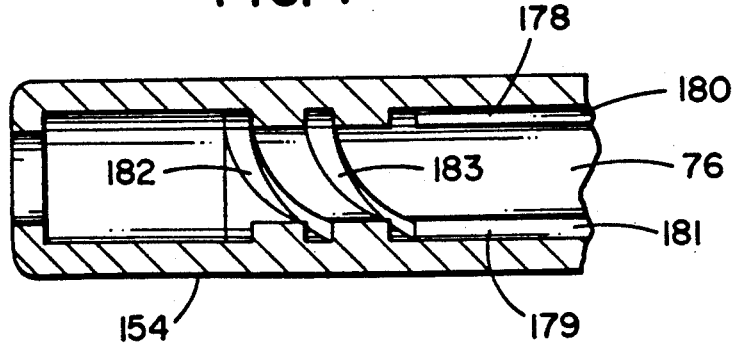
FIG. 7 is a cross sectional side view of an outer electrode used in an alternate embodiment of the present invention having both straight grooves and helical grooves for cooperating with a portion of the inner electrode to limit or control axial rotation thereof.

Referring to FIG. 7, there is shown a cross-sectional view of an outer electrode body 154 for an alternate embodiment of the invention. In the embodiment shown, the grooved channel portion 76 has two grooves 178 and 179 that have straight portions 180 and 181 and helical portions 182 and 183. In this embodiment, the straight portions 182 and 183 can prevent axial rotation of the inner electrode when lock pin ends are located therein and, the helical portions 180 and 181 can allow the inner electrode to rotate, but only at a predetermined rate relative to longitudinal advancement. However, any suitable types of grooves or locking engagement between the inner and outer electrodes may be provided.

It should be understood that the foregoing description is only illustrative of the invention. Various alternatives and modifications can be devised by those skilled in the art without departing from the spirit of the invention. Accordingly, the present invention is intended to embrace all such alternatives, modifications an variances which fall within the scope of the appended claims.

What is claimed is:

1. A cardiac lead assembly comprising:
 a first conductor;
 a first electrode having a conduit therein having a lock groove within said conduit, said first electrode being connected to a distal end of said first conductor;

a second electrode having a fixation bobbin, a fixation screw fixedly connected to said fixation bobbin and a lock pin extending from said fixation bobbin, said second electrode being longitudinally movable within said first electrode conduit when in a first position wherein said lock pin and said lock groove substantially prevents axial rotation of said second electrode relative to said first electrode and in a second position wherein said second electrode is capable of axial rotation relative to said first electrode; and a torsion coil having a first distal end fixedly connected to said fixation bobbin and an opposite second end, said coil ends being axially rotatable relative to each other for storing torsional potential energy while said second electrode is at said first position and for releasing stored torsional energy to axially rotate said second electrode at said second position, said coil having a coil channel therein for passage of a stylet therethrough for manually pushing and longitudinally moving said second electrode from said first position to said second position such that, upon movement of said second electrode to said second position, said stored torsional energy can be, at least partially, released for axially rotating said coil first distal end and second electrode, a tip of said second electrode fixation screw can penetrate a surface of a patient's heart, and said fixation screw can automatically screw said second electrode into the patient's heart as said second electrode rotates thereby embedding and fixing the lead with the heart.

2. An assembly as in claim 1 wherein said first conductor is comprised of a tubular coiled member.

3. An assembly as in claim 1 wherein said torsion coil is comprised of an electrically conductive material for functioning as a conductor for said second electrode.

4. An assembly as in claim 1 wherein said first electrode comprises a back stop member having said first conductor connected thereto and having a channel for passage of said coil and a stylet therethrough.

5. An assembly as in claim 1 wherein said lock pin extends from opposite sides of said fixation bobbin.

6. An assembly as in claim 5 wherein said first electrode has two lock grooves for receiving opposite ends of said lock pin.

7. An assembly as in claim 1 wherein said first electrode has a distal tip with an aperture therein for movement of said fixation screw therethrough.

8. An assembly as in claim 7 wherein a portion of said second electrode is engageable with a portion of said first electrode at said second position for retaining said first electrode distal tip against the surface of a patient's heart.

9. An assembly as in claim 1 wherein said first electrode has an enlarged portion of said conduit for relatively free rotational movement of said second electrode therein.

10. An assembly as in claim 1 wherein said fixation bobbin is comprised of a dielectric member and a conductive pin passing therethrough for electrically connecting said coil to said fixation screw, said dielectric member substantially insulating and separating conductive portions of said second electrode from said first electrode at said second position.

11. An assembly as in claim 1 wherein said second electrode has a keyed portion for a stylet tip such that an operator can control the release of stored torsional energy.

12. An assembly as in claim 1 further comprising means for automatically proportionally releasing stored torsional energy relative to longitudinal movement of said second electrode.

13. A cardiac lead assembly comprising:
a first electrode;
a second electrode at least partially located in said first electrode and having a corkscrew-type fixation tip;
means for conducting electricity to and from said first and second electrodes;
means for allowing access to a rear end of said second electrode by a stylet for manually pushing said second electrode and longitudinally moving said second electrode relative to said first electrode; and
means for automatically axially rotating said second electrode upon movement of said second electrode from a first longitudinal position to a second longitudinal position to thereby automatically screw said fixation tip into a heart of a patient.

14. An assembly as in claim 13 wherein said means for automatically axially rotating can, at least partially, axially rotate said second electrode at a rate proportional to longitudinal movement of said second electrode relative to said first electrode.

15. An assembly as in claim 13 further comprising means for preventing axial rotation of said second electrode at said first position.

16. An assembly as in claim 13 wherein said means for axially rotating said second electrode comprises a coiled inner conductor that can exert a torsional force on said second electrode and thereby turn said second electrode.

17. A method for attaching an electrical lead to a patient's heart comprising the steps of:
providing a cardiac lead assembly which comprises a first electrode, a second electrode with a screw tip, means for automatically axially rotating the second electrode, and means for restraining axial rotation of the second electrode;
pointing a distal end of the assembly at a selected portion of a patient's heart;
longitudinally moving the second electrode relative to the first electrode manually with a stylet to a location wherein the second electrode screw tip contacts a patient's heart and the means for restraining axial rotation of the second electrode is disengaged; and
automatically axially rotating the second electrode such that the second electrode screw tip can penetrate a surface of the heart and screw the second electrode into a fixedly embedded position in the heart.

18. A method as in claim 17 further comprising the step of torsionally twisting an inner coil conductor of the lead assembly prior to pointing a distal end of the assembly at a selected portion of a patient's heart.

* * * * *